United States Patent [19]

Spicer et al.

[11] 3,953,506
[45] Apr. 27, 1976

[54] UREIDOTETRALIN COMPOUNDS

[75] Inventors: Larry Dean Spicer, Princeton;
Joseph Michael Pensack, Trenton;
Robert Daniel Wilbur, Titusville, all of N.J.; Gary Michael Demkovich, deceased, late of Cranbury, N.J., by Ruth Ellen Demkovich, executrix

[73] Assignee: American Cyanamid Company, Stamford, Conn.

[22] Filed: Feb. 7, 1974

[21] Appl. No.: 440,625

[52] U.S. Cl. .................. 260/553 A; 71/90; 71/94; 71/103; 71/105; 71/120; 260/256.4 N; 260/256.5 R; 260/294.8 C; 260/295 F; 260/306.7 T; 260/306.8 R; 260/453 R; 260/465 D; 260/465 E; 260/552 R; 260/553 C; 424/251; 424/263; 424/273; 424/309; 424/322
[51] Int. Cl.$^2$............... C07C 127/19; C07C 157/09
[58] Field of Search ......... 260/553 A, 553 R, 453 R

[56] References Cited
UNITED STATES PATENTS

| | | | |
|---|---|---|---|
| 2,136,177 | 11/1938 | Carothers et al. | 260/553 A X |
| 2,276,174 | 3/1942 | Fleischhauer et al. | 260/553 A X |
| 2,537,138 | 1/1951 | Jennings | 260/553 A X |
| 2,723,193 | 11/1955 | Todd | 260/553 A X |
| 2,811,529 | 10/1957 | Bloom | 260/553 A X |
| 2,870,159 | 1/1959 | Bloom | 260/553 A X |
| 2,889,351 | 6/1959 | Bloom | 260/553 A X |
| 2,956,072 | 10/1960 | Bloom | 260/553 A X |
| 3,432,600 | 3/1969 | Harvey, Jr. | 260/553 A X |

FOREIGN PATENTS OR APPLICATIONS 1,081,887    5/1960    Germany ...................... 260/553 A

OTHER PUBLICATIONS

Kirsten et al., CA 56:432c (1961).
"Transformation of Tetrahydronaphthalene(tetralin) in the Animal Body," Schroeter et al., CA 13:43 (1919).
"2-[1-(1,2,3,4-Tetrahydronephthyl)]aminoimidazoline," Thomae, CA 59:P10065g (1963).
"Tetrahydro-α-naphthylharnstaff," Schroeter, Beilsteim, Vol. 12I, pp. 513, 514.

Primary Examiner—Robert V. Hines
Assistant Examiner—Thomas A. Waltz
Attorney, Agent, or Firm—Edward A. Conroy, Jr.

[57] ABSTRACT

This invention relates to ureidotetralin compounds and derivatives and selected enantiomers thereof. This invention also relates to methods for the preparation of said compounds which are useful as animal growth regulators and/or herbicidal agents.

6 Claims, No Drawings

UREIDOTETRALIN COMPOUNDS

SUMMARY OF THE INVENTION

This invention relates to compounds of the structure:

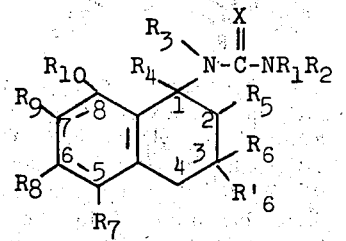

(I)

wherein X is a member selected from the group consisting of sulfur and oxygen; $R_1$ is a member selected from the group consisting of hydrogen, alkyl $C_1$–$C_{12}$, alkoxy $C_1$–$C_4$, allyl, benzyloxy, carboalkoxy ($C_1$–$C_4$)methyl, alkoxy($C_1$–$C_4$)methyl, cycloalkyl $C_3$–$C_7$, benzyl, hydroxy, hydroxyalkyl $C_1$–$C_4$, monohalophenyl, monoalkoxy($C_1$–$C_4$)phenyl, 2-thiazoyl, 2-thiazolinyl, 2-pyridinyl, 2-dihalopyrimidinyl, pyridinylmethyl, acetyl, benzoyl, amino, dialkyl($C_1$–$C_4$)amino, alkyl($C_1$–$C_4$)carbamoyl, anilino, alkyl($C_1$–$C_4$)phenylsulfonyl, phenylsulfonyl, 1,2,3,4-tetrahydro-1-naphthyl, and 2-[3-(1,2,3,4-tetrahydro-1-naphthyl)ureido]ethyl; $R_2$ is a member selected from the group consisting of hydrogen and alkyl $C_1$–$C_4$; $R_3$ is a member selected from the group consisting of hydrogen, alkyl $C_1$–$C_4$ and hydroxy; $R_4$ is a member selected from the group consisting of hydrogen and methyl; $R_5$ is a member selected from the group consisting of hydrogen and iodo; $R_6$ and $R'_6$ are each hydrogen or each methyl; $R_7$ is a member selected from the group consisting of hydrogen, amino, chloro, cyano, alkyl $C_1$–$C_4$ and alkoxy $C_1$–$C_4$; $R_8$ is a member selected from the group consisting of hydrogen, chloro, alkyl $C_1$–$C_4$ and alkoxy $C_1$–$C_4$; $R_9$ is a member selected from the group consisting of hydrogen, chloro, alkyl $C_1$–$C_4$, alkoxy $C_1$–$C_4$, acetamido and —NH—CO—NHR$_{11}$ where $R_{11}$ is allyl, alkyl $C_1$–$C_{12}$ or hydrogen; $R_{10}$ is a member selected from the group consisting of hydrogen, alkoxy $C_1$–$C_4$ and alkyl $C_1$–$C_4$; with the following provisos:

a that when $R_1$ is hydrogen, $R_2$ and $R_3$ may be alkylene group $C_2$–$C_4$ joined to form a ring;

b that when R groups $R_2$ to $R_{10}$ are hydrogen, then $R_1$ is a member other than hydrogen;

c that when $R_3$ is hydroxy then $R_1$ is a member other than hydroxy or alkoxy $C_1$–$C_4$;

d that when $R_1$ is hydroxy or alkoxy $C_1$–$C_4$, then X is oxygen and $R_3$ is hydrogen or alkyl $C_1$–$C_4$;

e that at least four of R groups $R_4$ to $R_{10}$ are hydrogen.

This invention also relates to the optically active forms of the compounds identified by the above structure. These forms are designated as the (R) and (S) isomers, with the (S) isomers generally being preferred since they appear to be biologically more active than the (R) forms. The preferred (S) isomers can be illustrated as follows:

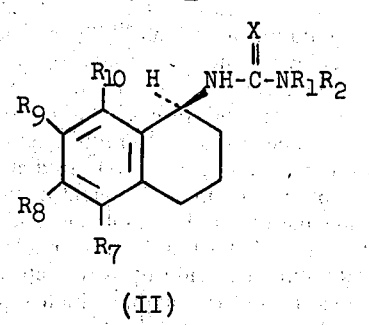

(II)

wherein X is sulfur or oxygen; $R_1$ is alkyl $C_1$–$C_4$, alkoxy $C_1$–$C_4$, benzyl or benzyloxy; $R_2$ is hydrogen or alkyl $C_1$–$C_4$; and at least two of the R groups selected from $R_7$, $R_8$, $R_9$ and $R_{10}$ are hydrogen; and the remaining R groups are selected from the group consisting of hydrogen, alkyl $C_1$–$C_4$ and alkoxy $C_1$–$C_4$.

The (R) isomers corresponding to the above-identified (S) isomers can be illustrated as follows:

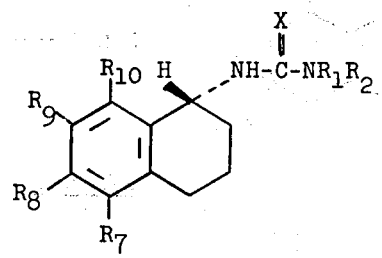

(III)

wherein X, $R_1$, $R_2$, $R_7$, $R_8$, $R_9$ and $R_{10}$ are as defined for said (S) isomer.

These optically active ureas have the same absolute configuration at the 1-position of the 1,2,3,4-tetrahydronaphthylene as the 1,2,3,4-tetrahydro-1-naphthylamine used as starting material. In order to obtain the desired (S) form of the urea, it is necessary to start with the (S) isomer of the 1-amino-1,2,3,4-tetrahydronaphthalene, which can be reacted with an isocyanate to form the (S) urea directly or with phosgene to yield the (S) isomer of the isocyanate, which is then reacted with an $R_1R_2$NH amine to yield an identical product.

The resolved 1,2,3,4-tetrahydro-1-naphthylamines have been reported in the published literature [R. Weidmann and J. P. Guette, Comptes Rendus des Seances de l'Academie des Sciences 268: 2225 (1969)] as resulting from the Curtius reaction with the optically active 1,2,3,4-tetrahydronaphthalene carboxylic acid azides. This work establishes the absolute configuration of the (R) and (S) isomers, but does not suggest the tetrahydronaphthylureas of the present invention, nor provides a practical preparative method for preparing the isomers in a high state of purity.

In accordance with this invention, we have developed several preferred routes of preparation for selected tetrahydronaphthylureas of the present invention. These preferred routes are identified as Methods A, B, C, D, E and F below, and methods for the preparation of specific compounds are also given in the Examples 1 through 111.

We have also found that 1,2,3,4-tetrahydro-1-naphthylamine and selected derivatives thereof can be separated into their optical isomers, as represented by formulas II and III, through the appropriate N-benzoyl glutamic acid salt. The (S)-(+)-1,2,3,4-tetrahydro-1- napthylamine forms a water-insoluble salt with (+)-N-benzoyl (R)-glutamic acid which can be crystallized out in high yield while the (R)-amine salt stays in solution. It is not necessary to employ more than about 1 mole of the resolving acid for each 2 moles of racemic amine, as a cheaper acid, preferably acetic, can be substituted for the balance of the required acid. In this way it is possible to obtain a high yield of the desired (S)-(+) amine based on the resolving acid. The resolved salt, (S)-1,2,3,4-tetrahydro-1-naphthylamine N-benzoyl (R)-glutamic acid salt, is treated with alkali which liberates the (S)-(+) amine which separates as an insoluble phase. It can be mechanically separated from the aqueous layer or extracted with a suitable solvent.

The process of Methods A through F may be graphically illustrated as follows:

Compounds having the structure:

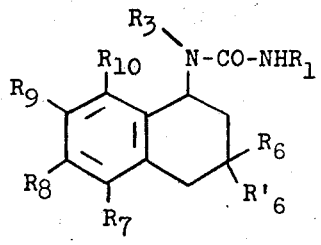

wherein $R_1$ is hydrogen, alkyl $C_1$–$C_{12}$, allyl, monohalophenyl, monoalkoxy($C_1$–$C_4$)phenyl, alkyl($C_1$–$C_4$)phenylsulfonyl, benzyl, cycloalkyl $C_3$–$C_7$, benzoyl, alkyl($C_1$–$C_4$) carbamoyl or 2-dihalopyrimidinyl; and $R_3$, $R_6$, $R'_6$, $R_7$, $R_8$, $R_9$ and $R_{10}$ are as described above; are preferably prepared by the process of Method A, illustrated above. This process involves

METHOD A

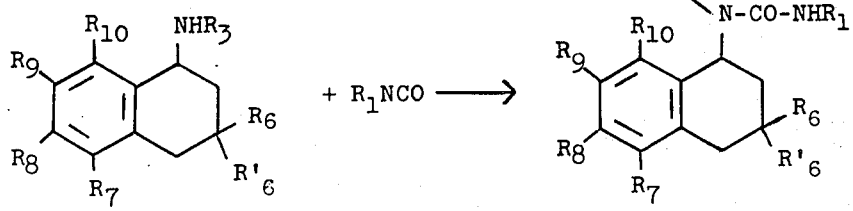

METHOD B

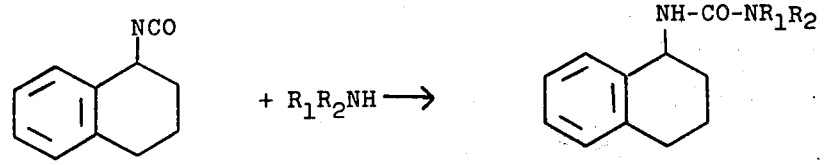

METHOD C

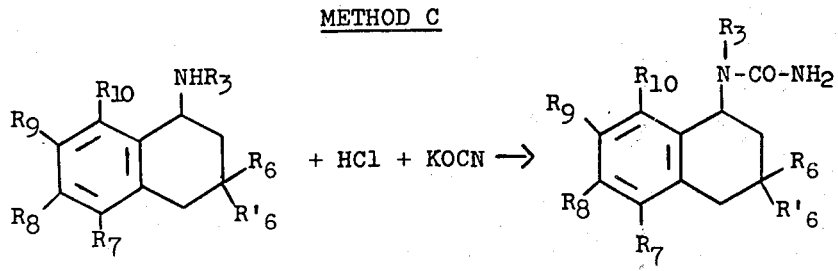

METHOD D

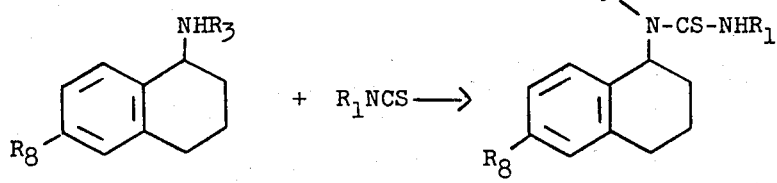

METHOD E

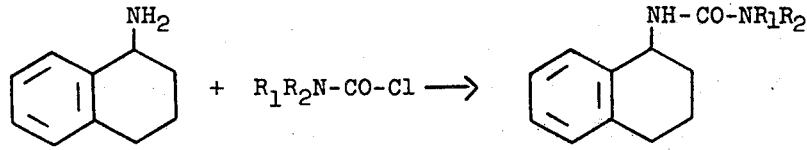

METHOD F

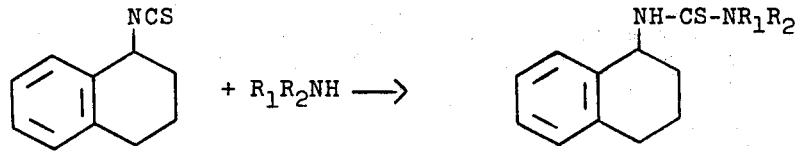

reacting approximately equimolar amounts of the appropriate tetrahydronaphthylamine or tetrahydronaphthylhydroxylamine with the appropriate isocyanate. This reaction is preferably conducted at a temperature in the range of from 0°C. to 100°C., and in the presence of an aprotic solvent such as a loweralkyl($C_1$-$C_6$)ketone, an ether such as tetrahydrofuran, or an aromatic solvent such as benzene or toluene. Also, when the naphthylamine contains a second amino group and the process of Method A is used, two mole equivalents of the isocyanate per mole of tetrahydronaphthylamine is required.

Where it is desirable to prepare compounds of the present invention of the structure:

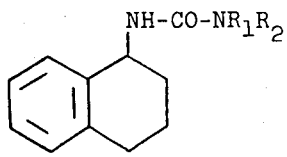

wherein $R_1$ is hydroxy, alkoxy $C_1$-$C_4$ or benzyloxy and $R_2$ is hydrogen or alkyl $C_1$-$C_{12}$, the process of Method B is a preferred route of preparation. This process involves the reaction of from about 1.0 to 2.0 equivalents of the appropriate hydroxylamine hydrohalide or alkoxyamine hydrohalide with tetrahydronaphthyl isocyanate. The reaction is generally carried out at a temperature between about 0°C. and 50°C., preferably 0°C. to 25°C., in the presence of an aprotic solvent and a tertiary-amine such as trimethylamine, triethylamine, pyridine, or the like.

The process of Method B may also be employed to prepare compounds having the above structure, wherein $R_2$ is hydrogen and $R_1$ is acetyl, hydroxyalkyl $C_2$-$C_4$, cycloalkyl $C_3$-$C_7$, dialkyl($C_1$-$C_4$) amino, anilino, 2-thiazolyl, 2-thiazolinyl, 2-pyridinyl, pyridinylmethyl, 1,2,3,4-tetrahydro-1-naphthyl or 2[3-(1,2,3,4-tetrahydro-1-naphthyl)ureido]ethyl. For these compounds, preparation involves reaction of 1,2,3,4-tetrahydro-1-naphthyl isocyanate with the appropriate amine, amide, hydrazine or hydrazide, and reactions are generally conducted in the presence of an aprotic solvent such as aromatic solvents ethers, loweralkylketones, chlorinated hydrocarbons, or the like, at a temperature between about 0°C. and 100°C., using approximately equimolar amounts of the isocyanate and the amine, amide, hydrazine or hydrazide.

The preferred method for the preparation of compounds of the formula:

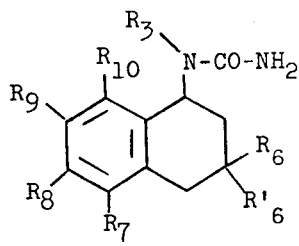

where $R_3$, $R_6$, $R'_6$, $R_7$, $R_8$, $R_9$ and $R_{10}$ are as described above, is the process of Method C. This process involves the reaction of approximately equimolar amounts of an appropriate tetrahydronaphthylamine, a mineral acid preferably hydrochloric, sulfuric or hydrobromic acid, and an alkali metal isocyanate, preferably potassium or sodium cyanate. The reaction is preferably carried out at a temperature between about 0°C.

and 80°C. in water or an aqueous-alcoholic solvent; and lower alcohols such as methanol, ethanol, isopropanol, butanol, and the like, typify those alcohols which may be used in the latter-named solvent systems.

Where the starting tetrahydronaphthylamine contains two amine groups, two equivalents of isocyanic acid should be employed in order to assure reaction at both amino functions. If, however, only one equivalent of isocyanic acid is used with the diaminotetrahydronaphthalene, it will be found that reaction takes place preferentially at the more basic amine function, i.e., generally the amine attached to the saturated ring.

Preparation of compounds represented by the formula:

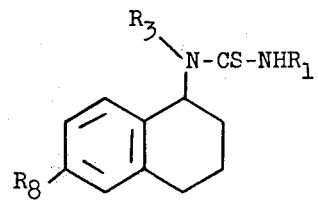

wherein $R_1$ is alkyl $C_1$-$C_{12}$ or benzoyl; $R_3$ is hydrogen, hydroxy or alkyl $C_1$-$C_4$; and $R_8$ is hydrogen or alkoxy $C_1$-$C_4$; are preferably prepared by the process of Method D which involves reaction of the appropriate tetrahydronaphthylamine, amino- or (hydroxylamino)-tetrahydronaphthylamine with an appropriate alkyl isothiocyanate. This reaction is generally conducted with an excess of the isothiocyanate (i.e., between about 1 and 2 mole equivalents of isothiocyanate per mole of tetrahydronaphthylamine), in the presence of an appropriate solvent such as an ether, alcohol, chlorinated hydrocarbon or aromatic solvent, at a temperature between about 0°C. and 100°C.

Compounds represented by the formula:

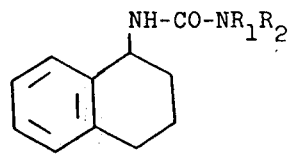

wherein $R_1$ and $R_2$ are each alkyl $C_1$-$C_{12}$, can be prepared by the process of Method E. This process involves the reaction of 1,2,3,4-tetrahydro-1-naphthylamine with an equimolar amount or slight excess, i.e., up to 20% excess, of an appropriate dialkylcarbamyl halide, preferably a dialkylcarbamyl chloride. The reaction is preferably conducted in the presence of an aprotic solvent such as described in Method A, at a temperature between about 0°C. and 100°C. It is also preferably to provide, in this reaction mixture, an amount of tertiary-amine approximately equivalent to the carbamyl halide used.

The process of Method F may be employed to prepare compounds of the present invention having the structure:

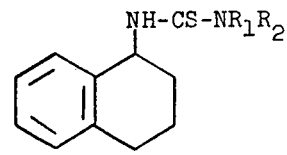

wherein $R_1$ is hydroxy, alkoxy $C_1$-$C_4$ or benzyloxy, and $R_2$ is hydrogen or alkyl $C_1$-$C_{12}$. This process involves the reaction of 1.0 to 2.0 equivalents of the appropriate hydroxylamine hydrohalide or alkoxyamine hydrohalide with 1,2,3,4-tetrahydro-1-naphthyl isothiocyanate. The reaction is generally carried out at a temperature between 0°C. and 60°C., preferably 20°C. to 40°C., in the presence of a protic or aprotic solvent and a tertiary-amine such as trimethylamine, triethylamine, pyridine, or the like. The process of Method F is also applicable for the preparation of compounds of the above structure, wherein $R_2$ is hydrogen or alkyl $c_1-C_{12}$ and $R_1$ is alkyl $C_1-C_{12}$, allyl carboalkoxy($C_1-C_4$)methyl, cycloalkyl $C_3-C_7$, benzyl, hydroxyalkyl $C_2-C_4$, monohalophenyl, monoalkoxy($C_1-C_4$)phenyl, pyridinylmethyl, dialkyl($C_1-C_4$)amino, alkyl($C_1-C_4$)carbamoyl, anilino, 1,2,3,4-tetrahydro-1-naphthyl,, and 2-[3-(1,2,3,4-tetrahydro-1-naphthyl)ureido]ethyl.

This process involves the reaction of approximately equimolar amounts of 1,2,3,4-tetrahydro-1-naphthyl isothiocyanate and a compound having the formula: $R_1R_2NH$ in the presence of a protic or aprotic solvent at a temperature between about 0°C. and 80°C. Reaction of two molar equivalents of the tetrahydronaphthyl isothiocyanate with a diamine gives the bis-thiourea product.

The compounds of this invention are useful as herbicidal agents effective for the control of a wide variety of undesirable broadleaf weeds and grass weeds. Certain of said compounds are also useful for accelerating the growth rate of animals and for improving feed efficiency in the raising thereof.

As herbicidal agents, the active compounds may be applied to the foliage of undesirable plants or to soil containing seeds of undesirable plants. They may be applied in solid or liquid form, but are preferably applied in a liquid spray; as for example, as a wettable powder, emulsifiable concentrate or flowable composition which is dispersed in water or other inexpensive diluent, and applied to the foliage or soil in dilute solution. In practice, generally about 0.13 pound to 10 pounds per acre of the active compound will provide control of undesirable plants.

Wettable powders can be prepared by grinding together from about 25% to 75% by weight of the active compound, and from about 20% to 71.5% by weight of a finely divided carrier such as attapulgite, kaolin, silica, or the like. To this mixture is then added about 1.5% to 3.0% by weight of a surfactant such as a sodium N-methyl-N-oleoyl taurate ester of sodium isothionate, an alkyl phenoxy polyoxyethylene ethanol, or the like, and from about 2% to 3% by weight of a dispersant such as a highly purified sodium lignosulfonate, naphthalene sulfonic acid condensate, or the like.

Emulsifiable concentrates can be prepared by dissolving the active compound (about 25% to about 75% by weight), in an organic solvent such as acetone, methylisobutylketone, xylene or toluene, or mixture thereof, and adding thereto about 1% to 5% by weight of an emulsifier and, optionally, about 1% to about 5% by weight of a dispersant such as sodium lignin sulfonate.

Compounds of the present invention that are especially useful as preemergence herbicidal agents are represented by the structure identified as formula I above; wherein $R_1$ is hydrogen, alkyl $C_1-C_{12}$, alkoxy $C_1-C_4$, anilino, alkoxy $C_1-C_4$ methyl or allyl; $R_2$ is hydrogen or alkyl $C_1-C_4$; X is sulfur or oxygen (preferably oxygen); $R_3$ is hydrogen or methyl (preferably hydrogen); $R_7$ and $R_9$ are each separately hydrogen or methyl; $R_8$ is hydrogen or alkoxy $C_1-C_4$; and $R_4$, $R_5$, $R_6$, $R'_6$ and $R_{10}$ are hydrogen; with the proviso that at least one of $R_1$, $R_2$, $R_7$, $R_8$ and $R_9$ is a member other than hydrogen.

Compounds of the present invention which are particularly effective as animal growth promoting agents are represented by formula I above, wherein X is sulfur or oxygen (preferably oxygen); $R_1$ is alkyl $C_1-C_4$, alkoxy $C_1-C_4$, benzyl or benzyloxy; $R_2$ is hydrogen or alkyl $C_1-C_4$; $R_3$, $R_4$, $R_5$, $R_6$, $R'_6$ and $R_{10}$ are hydrogen; $R_7$ is hydrogen, alkyl $C_1-C_4$ or alkoxy $C_1-C_4$; $R_8$ is hydrogen, alkyl $C_1-C_4$ or alkoxy $C_1-C_4$; and $R_9$ is hydrogen or alkyl $C_1-C_4$.

As animal growth promoting agents, the active compounds can be administered to said animals incorporated in their diet, implanted in the form of one or several pellets under the skin of the animal, or injected subcutaneously or intramuscularly in the form of a paste, solution or suspension.

When administered with the animal diet, generally about 25 ppm. to 800 ppm., and preferably 50 ppm. to 200 ppm., of the drug is effective for increasing weight gains of the treated animals. It is, of course, obvious that the drug may be formulated as a premix, supplement or concentrate, with other edible carriers such as ground corn, soybean meal, fish meal, and the like, and then mixed with or added to the animal feed at the feeding site. In such concentrate formulations, the drug may amount to from about 1% to 30% by weight of the formulation.

The drug may also be prepared as a pellet for implanation under the animal's skin. Usually, about a 1:1 or higher ratio of the drug and a pharmaceutically acceptable carrier such as castorwax are blended. The blended material is then pressed into the form of a pellet, which is introduced singly or in multiple doses with a pellet injector under the animals's skin. The pellet generally contains about 5 mg. to 100 mg., and preferably 10 mg. to 50 mg., of the ureidotetralin, which is slowly released into the animal's system following implantation. With this method of application, the drug can be administered at periodic intervals throughout the feeding period of the animals. Formulations and intervals between implantations can be varied to provide a daily drug release of generally about 0.005 mg. to 0.5 mg. per kg. of animal body weight, and preferably 0.01 mg. to 0.2 mg. per kg. of animal body weight.

SPECIFIC DISCLOSURE

The present invention may be further understood by referring to the examples set forth below which are provided simply by way of illustration, and are not intended to limit the invention.

EXAMPLES 1 through 49

Preparation of 1-Ethyl-3-(1,2,3,4-tetrahydro-1-naphthyl)urea

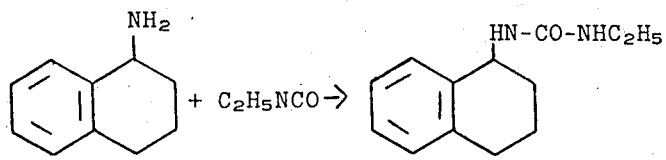

To a solution containing 7.4 grams (0.05 mole) of 1,2,3,4-tetrahydro-1-naphthylamine in 150 ml. anhydrous ether is added dropwise with stirring 3.6 grams (0.05 mole) ethyl isocyanate in 10 ml. ether. After the addition, the mixture is heated under reflux for 3 hours, the mixture cooled, and the solid collected by filtration. Recrystallization of the crude product from aqueous methanol gives analytically pure 1-ethyl-3-(1,2,3,4-tetrahydro-1-naphthyl)urea, melting point 178°C. to 179°C. Other aprotic solvents such as acetone, tetrahydrofuran and benzene may be used as solvents for this reaction. Temperatures employed for the reaction are in the range of 0°C. to 100°C.

The N'-substituted ureas listed in Table I below are generally prepared in a similar way using the appropriate tetrahydronaphthylamine or tetrahydronaphthylhydroxylamine and appropriate isocyanate. When the naphthylamine contains a second amino group, two equivalents of isocyanate are usually used so that reaction occurs at both amine functions. However, it is also possible to obtain selective reaction of the more basic amine function of the diaminotetrahydronaphthalene using only one equivalent of isocyanate.

TABLE I

Compound Structure: 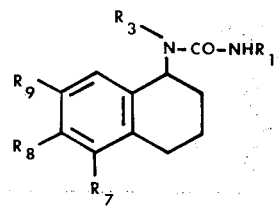

| Example Number | $R_1$ | $R_3$ | $R_7$ | $R_8$ | $R_9$ | Melting Point °C |
|---|---|---|---|---|---|---|
| 2 | $C_2H_5$ | $(CH_3)_2CH$ | H | H | $CH_3CONH$ | 238.5–240 |
| 3 | $C_2H_5$ | H | H | H | $C_2H_5NHCONH$ | 255–256.5 |
| 4 | $CH_2=CHCH_2$ | H | H | H | $CH_2=CHCH_2NHCO-NH$ | 234–234.5 |
| 5 | $CH_3$ | $(CH_3)_2CH$ | H | H | $CH_3CONH$ | 252–254 (dec.) |
| 6 | $C_{12}H_{25}$ | H | H | H | $C_{12}H_{25}NHCONH$ | 180–182 |
| 7 | $CH_3$ | H | H | H | $CH_3CONH$ | 243–243.5 |
| 8 | $C_2H_5$ | H | H | H | $CH_3CONH$ | 232.5–233 |
| 9 | $C_{12}H_{25}$ | H | H | H | $CH_3CONH$ | 206–207 |
| 10 | $CH_3$ | H | H | H | $CH_3NHCONH$ | 242.5–244 |
| 11 | $CH_3\text{-}C_6H_4\text{-}SO_2$ | H | H | H | H | 189–190 |
| 12 | $Cl\text{-}C_6H_4$ | H | H | H | H | 234–235 |
| 13 | $CH_3$ | H | H | H | H | 173–175 |
| 14 | $C_3H_7\text{-}n$ | H | H | H | H | 141–143 |
| 15 | $(C_2H_5)(CH_3)CH$ | H | H | H | H | 171–172 |
| 16 | H | H | $CH_3O$ | H | H | 225–226 |
| 17 | $C_2H_5$ | H | $CH_3O$ | H | H | 190–191 |
| 18 | $C_6H_5CH_2$ | H | H | H | H | 179–182 |
| 19 | $CH_3$ | H | H | $CH_3$ | $CH_3$ | 215–216 |
| 20 | $C_2H_5$ | H | H | $CH_3$ | $CH_3$ | 204–205.5 |
| 21 | $CH_3$ | H | $CH_3$ | H | $CH_3$ | 196–198 |
| 22 | $CH_3$ | H | $NH_2$ | H | H | 195–198 |
| 23 | $C_2H_5$ | H | $NH_2$ | H | H | 190–191 |
| 24 | $CH_3$ | H | Cl | H | H | 208–209 |
| 25 | $C_2H_5$ | H | Cl | H | H | 210–211 |
| 26 | $CH_3$ | H | CN | H | H | 209–210 |
| 27 | $C_6H_{11}$ | H | H | H | H | 202–204 |
| 28 | $-C_6H_4OCH_3$ | H | H | H | H | 215–216.5 |
| 29 | $CH_3$ | H | $CH_3O$ | H | H | 198–199 |
| 30 | $C_{12}H_{25}$ | H | $CH_3O$ | H | H | 132–134 |
| 31 | H | H | H | $CH_3O$ | H | 199.5–203 |
| 32 | $C_2H_5$ | H | H | $CH_3O$ | H | 165–170 |
| 33 | $CH_3$ | H | H | H | $(CH_3)_2CH$ | 179–180 |
| 34 | $C_2H_5$ | H | H | H | $(CH_3)_2CH$ | 156–158 |
| 35 | $C_{12}H_{25}$ | H | H | H | $(CH_3)_2CH$ | 90–93 |
| 36 | $C(CH_3)_3$ | H | H | H | $CH_3$ | 176–178 |
| 37 | $C_{12}H_{25}\text{-}n$ | H | H | H | H | 101–105 |
| 38 | $C_2H_5$ | H | $CH_3$ | H | $CH_3$ | 186–187 |
| 39 | $C_{12}H_{25}$ | H | $CH_3$ | H | $CH_3$ | 103–105 |
| 40 | $C_6H_{13}\text{-}n$ | H | H | H | H | 93–98 |
| 41 | $CH_2=CH-CH_2$ | H | H | H | H | 158–161 |

TABLE I-continued

Compound Structure:

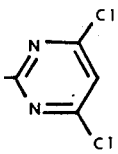

| Example Number | R₁ | R₃ | R₇ | R₈ | R₉ | Melting Point °C |
|---|---|---|---|---|---|---|
| 42 | C₁₂H₂₅ | H | H | CH₃ | CH₃ | 136–137 |
| 43 | CH₃ | H | H | CH₃ | CH₃ | 195–197 |
| 44 | CH₃O—(C₆H₄)—CH₂ | H | H | H | H | 156–158 |
| 45 | C₂H₅ | CH₃ | H | H | H | 110–113 |
| 46 | —CH₂—CO₂—C₂H₅ | CH₃ | H | H | H | oil |
| 47 | C₂H₅ | OH | H | H | H | 140–143 |
| 48 | —CH₂—CO₂—C₂H₅ | H | H | H | H | 138–140 |
| 49 | 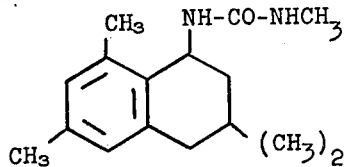 | | H | H | H | H | 206–213 |

EXAMPLE 50

Preparation of 1-Methyl-3-(1,2,3,4-tetrahydro-3,3,6,8-tetramethyl-1-naphthyl)urea Following the procedure of Example 1, but substituting the appropriate naphthylamine and isocyanate for 1,2,3,4-tetrahydro-1-naphthylamine and ethyl isocyanate, yields the subject compound having the structure:

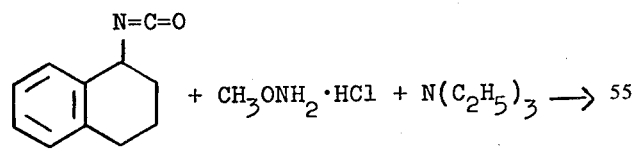

melting point 195.5°C. to 197°C.

EXAMPLES 51 through 56

Preparation of 1-Methoxy-3-(1,2,3,4-tetrahydro-1-naphthyl)urea

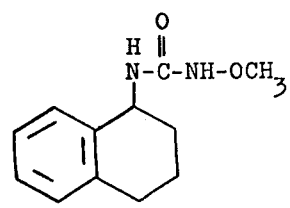

To an ice cold, stirred mixture of 6.7 grams (0.080 mole) of methoxyamine hydrochloride in 80 ml. of methylene chloride is added a solution of 8.1 grams (0.080 mole) of triethylamine in 20 ml. of methylene chloride. The mixture is stirred at 15°C. for 15 minutes, and is then allowed to warm to 15°C. to 25°C. while a solution of 6.94 grams (0.04 mole) of 1,2,3,4-tetrahydro-1-naphthyl isocyanate in 25 ml. of methylene chloride is added dropwise. The mixture is stirred for 30 minutes at room temperature and then filtered. The filtrate is washed with water, dried sodium sulfate, and the solvent evaporated at reduced pressure to give a solid. Recrystallization of the solid from acetone/hexane gives 6.75 grams of the product, melting point 122°C. to 125°C. Recrystallization of the product from acetone/hexane gives the analytical sample, melting point 123.5°C. to 125°C. Analysis Calculated for C₁₂H₁₆N₂O₂: C, 65.43; H, 7.32; N, 12.72. Found: C, 65.32; H, 7.33; N, 12.64.

The alkoxy- and hydroxyureas, described in Table II below, are prepared in a similar way using the appropriate hydroxyl- or alkoxyamine (1.0 to 2.0 equivalents) and tetrahydronaphthyl isocyanate. Other aprotic solvents may be used in this procedure. The conversion of the alkoxy- and hydroxylamine salts to the corresponding free bases may be accomplished with other bases such as potassium carbonate, sodium carbonate, as well as other trialkylamines.

TABLE II

Compound Structure:

| Example Number | R₁ | R₂ | Melting Point °C |
|---|---|---|---|
| 52 | OCH₃ | CH₃ | 62–64.5 |
| 53 | OH | H | 154–157 |
| 54 | OH | CH₃ | 105.5–108.5 |
| 55 | OC₂H₅ | H | 82–88 |
| 56 | OCH₂C₆H₅ | H | 90–93 |

EXAMPLES 57 through 68

Preparation of
1-Methyl-1-(1,2,3,4-tetrahydro-1-naphthyl)urea

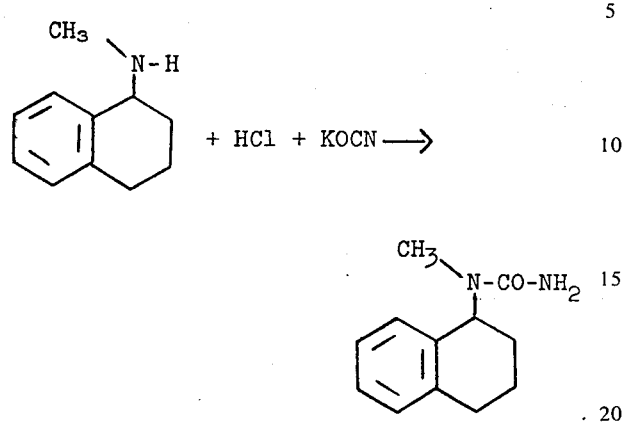

To a stirred solution of 8.05 grams (0.05 mole) of 1,2,3,4-tetrahydro-N-methyl-1-naphthylamine in 10 ml. of methanol is added a solution of 4.2 ml. of 12N hydrochloric acid (0.05 mole) in 35 ml. of water. The mixture is cooled in an ice-water bath while a solution of 4.46 grams (0.055 mole) of potassium cyanate in 15 ml. is added dropwise. After the addition is complete, the reaction mixture is stirred at room temperature for 45 minutes and then at 70°C. to 75°C. for 30 minutes. The mixture is cooled to 25°C., and the solid product filtered off, washed with water and then with cold ethyl acetate. The dried product weighs 7.1 grams and has melting point 160°–163°C. Recrystallization from acetone-hexane gives the analytical sample, melting point 161°C. to 163°C. Recrystallization from acetone-hexane gives the analytical sample, melting point 161°C. to 163°C. Analysis Calculated for $C_{12}H_{16}N_2O$: C, 70.56; H, 7.90; N, 13,72. Found: C, 70.60; H, 7.94; N, 13.75.

Following the above procedure and substituting the appropriate amine, the product ureas in Table III are prepared. The preformed amine salt, e.g., hydrochloride or bisulfate, may be substituted for the in situ preparation of the amine salt. The reaction can be conveniently carried out in water or aqueous alcohol solvent systems.

Where the starting amine has two amino groups, two equivalents of isocyanic acid may be used so that reaction occurs at both amino functions. However, it is also possible to obtain selective reaction of the more basic amine function of the diaminotetrahydronaphthalene using one equivalent of isocyanic acid.

TABLE III

Preparation of Compounds Having the Structure:

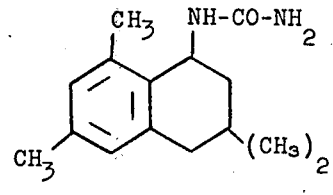

| Example Number | $R_3$ | $R_7$ | $R_8$ | $R_9$ | Melting Point °C |
|---|---|---|---|---|---|
| 58 | H | H | H | $H_2NCONH$ | 247–248 (dec.) |
| 59 | H | H | H | $CH_3CONH$ | 237 (dec.) |
| 60 | H | H | $CH_3O$ | H | 225–226 |
| 61 | H | $CH_3$ | H | $CH_3$ | 231–232 |
| 62 | H | $NH_2$ | H | H | 227–228 (dec.) |
| 63 | H | Cl | H | H | 241–242 (dec.) |
| 64 | H | CN | H | H | 248–249 (dec.) |
| 65 | H | H | $OCH_3$ | H | 199.5–203 |
| 66 | H | H | H | $(CH_3)_2CH$ | 200–201 (dec.) |
| 67 | H | H | $CH_3$ | $CH_3$ | 240–241 |
| 68 | H | H | Cl | Cl | 194–196 |

EXAMPLE 69

Preparation of
(1,2,3,4-Tetrahydro-3,3,6,8-tetramethyl-1-naphthyl)urea

The subject compound can be prepared by the process of Example 57 and substituting the appropriate amine for 1,2,3,4-tetrahydro-N-methyl-1-naphthylamine to yield a compound having the structure:

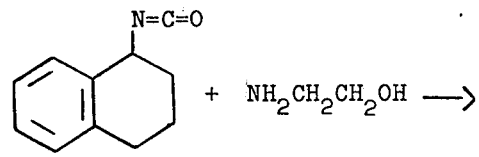

melting point 183.5°C. to 185°C.

EXAMPLES 70 through 84

Preparation of
1-(2-Hydroxyethyl)-3-(1,2,3,4-tetrahydro-1-naphthyl)urea

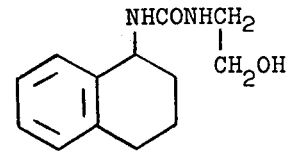

To a stirred solution of 2.42 grams (0.04 mole) of ethanolamine in 200 ml. of ether is added a solution of 6.95 grams (0.04 mole) of 1,2,3,4-tetrahydro-1-naphthyl isocyanate in 150 ml. of ether over a period of 30 minutes. Additional ether is added to facilitate stirring as the product precipitates. One hour after the isocyanate addition is complete, the mixture is filtered. The filter cake is washed with ether and dried to give 8.61 grams white solid, melting point 146°C. to 149°C. Recrystallization from nitromethane gives the analytical sample, melting point 147°C. to 149°C. Analysis calculated for $C_{13}H_{18}N_2O_2$: C, 66.64; H, 7.74; N, 11.96. Found: C, 66.35; H, 7.78; N, 11.90.

Following the above procedure and substituting for ethanolamine the appropriate amine, amide, hydrazine or hydrazide, the substituted ureas shown in Table IV, are prepared. Other aprotic solvents such as benzene, toluene, tetrahydrofuran, dimethylformamide, methylene chloride, chloroform and acetone are useful solvents in this procedure. Temperatures employed in this procedure range from 0°C. to 100°C. Reaction of two equivalents of the tetrahydronaphthyl isocyanate with a diamine (e.g., $NH_2CH_2CH_2NH_2$) gives the bis-urea product.

TABLE IV

Compound Structure: tetrahydronaphthyl-NH-CO-NR$_1$R$_2$

| Example Number | R$_1$ | R$_2$ | Melting Point °C |
|---|---|---|---|
| 71 | —NH—CO—OCH$_3$ | H | 166–168 |
| 72 | —N(CH$_3$)$_2$ | H | 146–148 |
| 73 | —NH—C$_6$H$_5$ | H | 167–169.5 |
| 74 | 2-(4,5-dihydrothiazolyl) | H | 110–114.5 |
| 75 | 2-pyridyl | H | 183–188 |
| 76 | 2-thiazolyl | H | 179–182 |
| 77 | —CH$_2$CH$_2$NH—CO—NH—(tetrahydronaphthyl) | H | 258–259 (dec.) |
| 78 | —CH$_2$—CH$_2$— | | 72–74 |
| 79 | —CH$_2$-(4-pyridyl) | H | 170–173.5 |
| 80 | —CH$_2$-(3-pyridyl) | H | 141–143 |
| 81 | —CH$_2$CH$_2$—N(CO—NH-tetrahydronaphthyl)—CH$_2$CH$_2$— | H | 290.5–293 (dec.) |
| 82 | —COCH$_3$ | H | 176.5–180.5 |

TABLE IV-continued

Compound Structure:

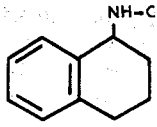

| Example Number | R₁ | R₂ | Melting Point °C |
|---|---|---|---|
| 83 | 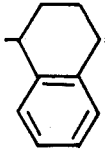 | H | 290–292 |
| 84 | $-NH-\overset{NH}{\underset{\|\|}{C}}-NH_2 \cdot p-CH_3-C_6H_4-SO_3H$ | H | 193–197.5 |

EXAMPLES 85 and 86

Preparation of
1,1-Dimethyl-3-(1,2,3,4-tetrahydro-1-naphthyl)-urea

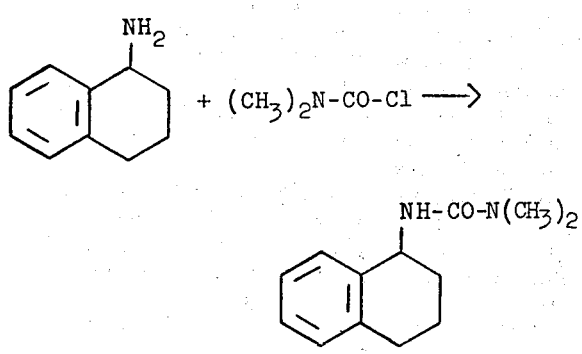

To a stirred mixture of 7.1 grams (0.05 mole) of 1,2,3,4-tetrahydro-1-naphthylamine, 7 ml. (0.05 mole) of triethylamine and 100 ml. of benzene is added, dropwise, 5.5 grams (0.05 mole) of dimethylcarbamyl chloride. The mixture is stirred for one day at ambient temperature and then filtered to remove triethylamine hydrochloride. The filter cake is washed with benzene. Evaporation of the filtrate at reduced pressure gives a white solid. The solid is recrystallized from toluene to give the product, melting point 139°C. to 140°C. Analysis calculated for $C_{13}H_{18}N_2O$: C, 71.53; H, 8.31; N, 12.83. Found: C, 71,82; H, 8.33; N, 12,29.

1,1-Diethyl-3-(1,2,3,4-tetrahydro-1-naphthyl)urea, melting point 86°C. to 87°C., is prepared by the above procedure by substituting diethylcarbamyl chloride for dimethylcarbamyl chloride.

EXAMPLES 87 through 91

Preparation of
1-Ethyl-3-(1,2,3,4-tetrahydro-1-naphthyl)-thio-urea

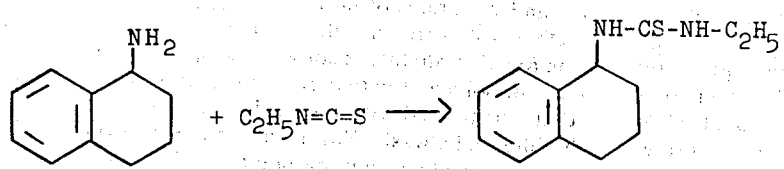

To a stirred solution of 8.84 grams (0.060 mole) of 1,2,3,4-tetrahydro-1-naphthylamine in 100 ml. of acetone, under a blanket of nitrogen, is added a solution of 6.27 grams (0.072 mole) of ethyl isothiocyanate in 50 ml. of acetone. The reaction mixture is stirred overnight, and the solvent then evaporated at reduced pressure. Toluene is added to the residue, and the mixture is then evaporated at reduced pressure. The residue is crystallized from nitromethane to give 7.08 grams of the product, melting point 120°C. to 122°C. Analysis calculated for $C_{13}H_{18}N_2S$: C, 66.62; H, 7.74; N, 11.96. Found: C, 66.38; H, 7.74; H, 11.86.

The thioureas listed in Table V are prepared by reaction of the appropriate amino- (or hydroxylamino-) tetrahydro-naphthylamine and alkyl isothiocyanate. Other solvents, e.g., ether, methylene chloride, ethanol, chloroform, tetrahydrofuran, benzene and toluene, may be also used.

TABLE V

Compound Structure:

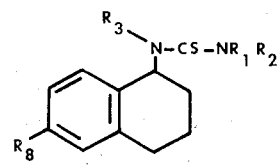

| Example Number | R₁ | R₂ | R₃ | R₈ | Melting Point °C |
|---|---|---|---|---|---|
| 88 | CH₃ | H | CH₃ | H | 104–109 |
| 89 | COC₆H₅ | H | H | H | 108–112 |
| 90 | C₂H₅ | H | H | OCH₃ | 127.5–131.5 |
| 91 | CH₃ | H | OH | H | 157–160.5 |

EXAMPLE 92

Preparation of 1-(1,2,3,4-Tetrahydro-1-naphthyl)-2-imidazolidinone

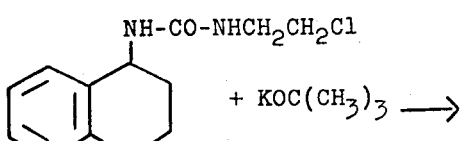
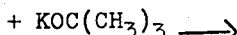
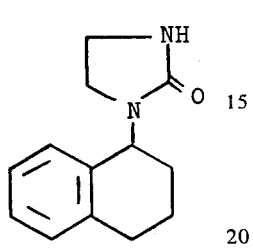

To a stirred solution of 3.8 grams (0.015 mole) of 1-(2-chloroethyl)-3-(1,2,3,4-tetrahydro-1-naphthyl)urea in 75 ml. dry tetrahydrofuran is added dropwise a solution of 2.25 grams (0.02 mole) of potassium tert-butoxide in 50 ml. of dry tetrahydrofuran under a nitrogen atmosphere. The reaction is then allowed to proceed at ambient temperature overnight. The mixture is then evaporated at reduced pressure. The residue is partitioned between water and ether. The ether layer is washed with water, dried, sodium sulfate, and evaporated at reduced pressure. Crystallization of the residue from acetone-ether-hexane gives 0.70 gram of product, melting point 134°C. to 139.5°C. Recrystallization from acetone-hexane gives the analytical sample, melting point 138°C. to 141.5°C. Analysis calculated for $C_{13}H_{16}N_2O$: C, 72.19; H, 7.46; N, 12.95. Found: C, 72.04; H, 7.43; N, 12.89.

EXAMPLE 93

Preparation of 1-Methyl-4([3-(1,2,3,4-tetrahydro-1-naphthyl)-ureido]methyl)pyridinium perchlorate

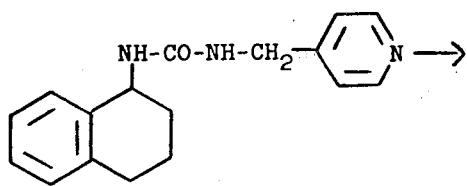
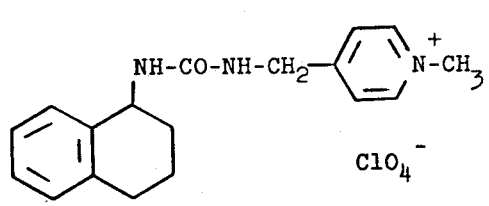

To a stirred solution of 4.0 grams (0.014 mole) of 1-(4-pyridylmethyl)-3-(1,2,3,4-tetrahydro-1-naphthyl)urea in 50 ml. of chloroform is added 2.3 (0.018 mole) of dimethyl sulfate in 25 ml. of chloroform. The reaction mixture is heated at reflux for 3.5 hours, cooled and the solvent removed at reduced pressure. The residue is triturated with ether and the ether solution is then decanted off. The residue is dissolved in water and treated with aqueous sodium perchlorate. The precipitate is filtered, washed with water and dried to give 4.2 grams of product, melting point 165°C. to 169°C. Recrystallization from water gives the analytical sample, melting point 166.5°C. to 169°C. Analysis calculated for $C_{18}H_{22}N_3ClO_5$: C, 54.62; H, 5.60; N, 10.62. Found: C, 54.62; H, 5.45; N, 10.66.

EXAMPLE 94

Preparation of 1-Cyano-3-(1,2,3,4-tetrahydro-1-naphthyl)urea

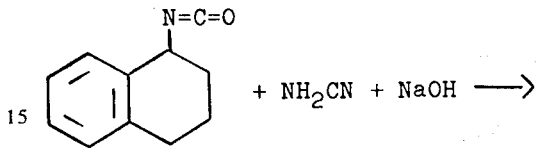
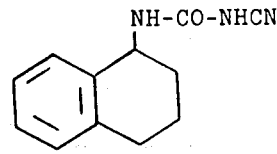

To a stirred solution of 3.36 grams (0.08 mole) of cyanamide and 1.2 grams of sodium hydroxide in 20 ml. of water, kept at 15°C., is added dropwise about one-half of 6.94 grams (0.04 mole) of tetrahydronaphthyl isocyanate. The mixture is then treated consecutively with a solution of 1.2 grams sodium hydroxide in 10 ml. of water and then the rest of the isocyanate. The mixture is stirred at 15°C. to 20°C. for an additional 30 minutes, diluted with 10 ml. water and the solution decanted from insoluble material. The solution is cooled with ice and acidified to the Congo red end point with 12N hydrochloric acid. The resultant precipitate is filtered, washed with water and dried to give 8.2 grams product, melting point 128°C. to 131°C. The analytical sample, obtained from acetone-hexane, has melting point 123°C. to 127°C. Analysis Calculated for $C_{12}H_{13}N_3O$: C, 66.95; H, 6.09; N, 19.52. Found: C, 66.67; H, 6.31; N, 19.73.

EXAMPLE 95

Preparation of 1-(Methoxymethyl)-3-(1,2,3,4-tetrahydro-1-naphthyl)urea

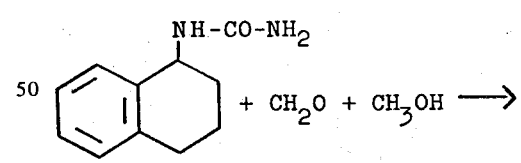
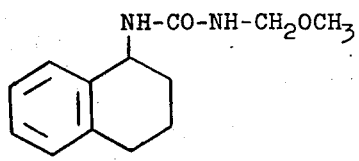

A solution of 7.6 grams (0.04 mole) of (1,2,3,4-tetrahydro-1-naphthyl)urea, 2.0 grams of sodium hydroxide and 2.2 grams of para-formaldehyde in 150 ml. of methanol is stirred at reflux temperature for 10 hours. The reaction mixture is cooled and neutralized with dry ice. The solvent is evaporated at reduced pressure. The residue is treated with water, the mixture filtered, and the filter cake washed with water and dried to give 8.2 grams of product, melting point 124.5°C. to 127.5°C.

Recrystallization from methyl isobutyl ketone gives the analytical sample, melting point 136°C. to 138.5° C.

EXAMPLE 96

Preparation of 4-(1,2,3,4-Tetrahydro-1-naphthyl)semicarbazide hydrochloride

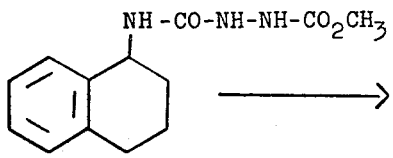

8.13 Grams (0.031 mole) of methyl 3-[(1,2,3,4-tetrahydro-1-naphthyl)carbamoyl]carbazate is added in portions to 31 ml. of stirred 4N potassium hydroxide maintained at 75°C. to 80°C. The mixture is stirred at this temperature for 30 minutes, then cooled in an ice bath and acidified with 12N hydrochloric acid. The precipitate is filtered, washed with cold water and then 2-propanol. The dried product weighs 1.88 grams and has melting point 189°C. to 191°C. The filtrate is evaporated under reduced pressure and the residue boiled in ethanol and filtered hot. The filtrate is evaporated at reduced pressure. The residue is crystallized from ethanol to give an additional 1.30 grams of product, melting point 191° C. to 193°C. Recrystallization from water gives the analytical sample, melting point 196°C. to 198°C. Analysis calculated for $C_{11}H_{16}N_3OCl$: C, 54.66; H, 6.67; N, 17.30. Found: C, 54.57; H, 6.69; N, 17.46.

EXAMPLE 97

Preparation of N-(5,6,7,8-Tetrahydro-8-isopropylamino-2-naphthyl)acetamide hydrochloride

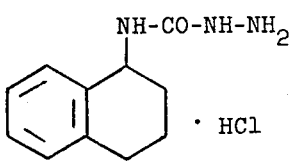

A mixture containing 9.0 grams (44 mmoles) of amine in 100 ml. dry acetone is shaken in an atmosphere of hydrogen at three atmospheres pressure in the presence of 1 gram of 5% palladium-on-carbon for 7.5 hours. The catalyst is removed by filtration and the solvent is removed under reduced pressure. The residue, consisting of essentially pure alkylated amine, is converted to its hydrochloride salt by adding an excess of 6N isopropanolic hydrogen chloride to an ether solution of the amine. The crystalline product, N-(5,6,7,8-tetrahydro-8-isopropylamino-2-naphthyl)acetamide hydrochloride, is recrystallized from 95% ethanol to give analytically pure product, melting point 252°C. to 253°C.

EXAMPLE 98

Preparation of (S)-1,2,3,4-Tetrahydro-1-naphthylamine N-Benzoyl-(R)-glutamic Acid Salt A stirred mixture of 284 grams (1.13 moles) of (R)-(+)-N-benzoylglutamic acid, 136 grams (2.26 moles) of acetic acid, and 2 liters of water is heated to 55°C. to give a solution. To this stirred solution is added 333 grams (2.26 moles) of racemic 1,2,3,4-tetrahydro-1-naphthylamine.

After an initial mild rise in reaction temperature, the crystalline salt precipitates. The mixture is stirred and allowed to cool over a period of about 1 hour. The mixture is cooled to 25°C., filtered, washed with cold ethanol and dried to give 396.3 grams of the (S)-1,2,3,4-tetrahydro-1-naphthylamine N-benzoyl-(R)-glutamic acid salt, melting point 204°C. to 210°C. The following rotations are obtained on the product:

[α]$_D^{28}$ −10.0° (c 3, HOAc)
[α]$_{436}^{28}$ −30.1° (c 3, HOAc)
[α]$_{365}^{28}$ −58.4° (c 3, HOAc)

EXAMPLE 99

Preparation of (R)-1,2,3,4-Tetrahydro-1-naphthylamine N-Benzoyl-(S)-glutamic Acid Salt Following the procedure of Example 98, but substituting N-benzoyl-(S)-glutamic acid for N-benzoyl-(R)-glutamic acid, yields the (R)-1,2,3,4-tetrahydro-1-naphthyl-amine N-benzoyl-(S)-glutamic acid salt. The melting point and yield of this product are the same as obtained in Example 6; however, the salt has an equal but opposite optical rotation.

EXAMPLE 100

Preparation of (S)-(+)-1,2,3,4-Tetrahydro-1-naphthylamine

A slurry of 130.3 grams (0.36 mole) of (S)-1,2,3,4-tetrahydro-1-naphthylamine N-benzoyl-(R)-glutamic acid salt in ice and water is made basic by the addition of a cold solution of 34.0 grams (0.847 mole) of sodium hydroxide in water. The liberated amine is extracted with ether. The ether solution is dried over a mixture of magnesium sulfate and sodium hydroxide pellets. The ether is evaporated, and the amine distilled to give the product boiling point 72°C. to 77°C. at 0.6 mm., [α]$_D^{25}$ +54.9° (c 5.2, benzene).

EXAMPLE 101

Preparation of (R)-(−)-1,2,3,4-Tetrahydro-1-naphthylamine

The (R) amine is made in the same way as described in Example 100, but from the salt from N-benzoyl-(S)-glutamic acid. It has [α]$_D^{25}$ −54.0° (c 5.1, benzene).

EXAMPLES 102 and 103

Preparation of (S)-(−)-1-Methyl-3-(1,2,3,4-tetrahydro-1-naphthyl)urea

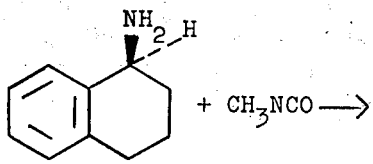

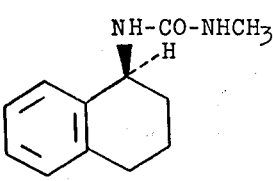

To a stirred solution of 17.7 grams (0.12 mole) of (S)-(+)-1,2,3,4-tetrahydro-1-naphthylamine in 500 ml. of ether, maintained under a nitrogen atmosphere, is added a solution of 8.0 ml. (0.135 mole) of methyl isocyanate in 250 ml. of ether over a 20-minute period. An additional 200 ml. of ether is added, and the mixture is stirred for 30 minutes. The mixture is filtered, and the filter washed with ether and then dried to give 23.3 grams of product, melting point 193°C. to 195°C. The following rotations are obtained on the product: [α]$_D^{25}$ −30.0° (c 5, HOAc); [α]$_{436}^{25}$ −73.0° (c 5, HOAc) and [α]$_{365}^{25}$ −136° (c 5, HOAc).

The (R)-(+) isomer corresponding to the above-identified (S)-(−) isomer is prepared in the same manner as above, starting with the (R)-(−)-1,2,3,4-tetrahydro-1-naphthylamine.

EXAMPLE 104

Preparation of (S)-(−)-1,2,3,4-Tetrahydro-1-naphthylurea

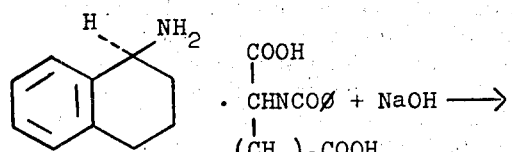

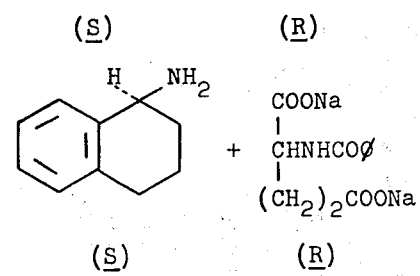

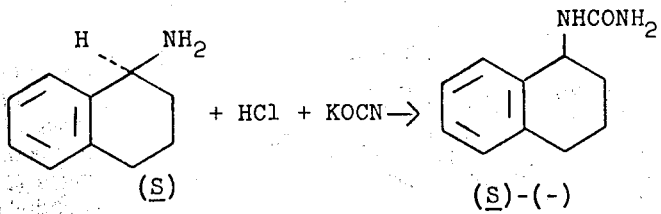

(S)-Amine-(R)-acid salt (1149 grams, 2.88 moles) is placed in a 12 liter separation funnel. Ice (300 grams) is added, followed by 346 grams (8.65 moles, 3 equivalents) of sodium hydroxide in 870 ml. of water. The mixture is shaken, and the liberated amine extracted with 4 liters of ether. The aqueous phase is extracted with an additional 2 liters of ether. The combined ether extracts are washed with saturated sodium chloride solution. The ether solution is then cooled with ice, and the amine extracted with 288 ml. of hydrochloric acid in 2 liters of water (3.46 moles of HCl, 20% excess). The ether layer is washed with 800 ml. of water. The combined aqueous phases containing the amine hydrochloride are placed in a 1 liter reaction flask. The reaction mixture is cooled to 5° C., and a solution of 280 grams (3.46 moles, 20% excess) of potassium cyanate in 1.5 liters of water is added through a dropping funnel. The cooling bath is removed, and the reaction mixture warmed to 70°C. to 80°C. The reaction mixture is then left standing overnight at room temperature. The urea is recovered by filtration, washed with water and then with cold isopropanol. The yield is 457 grams (2.40 moles, 83%), melting point 197°C. to 204°C., $[\alpha]_D^{25}$ −35.2° (c 5, HOAc); $[\alpha]_{436}^{25}$ −85.4° (c 5, HOAc).

EXAMPLE 105

Preparation of N-(1,2,3,4-Tetrahydro-1-naphthyl)hydroxylamine

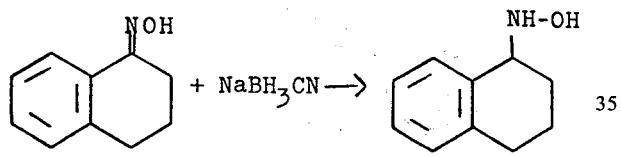

To a stirred solution of 16.12 grams (0.10 mole) of 1-tetralone oxime in 180 ml. of methanol is added 4.4 grams (0.07 mole) of sodium cyanoborohydride (NaBH$_3$CN) and 20 ml. of methanol. The solution is adjusted and maintained at ca. pH 3 to 4 with hydrogen chloride in ethanol. The reaction is allowed to proceed 4 hours at ambient temperature; an additional 2.2 grams of NaBH$_3$CN is added and the mixture kept at 45°C. for 3 hours. Now, 1 gram of NaBH$_3$CN is added and the solution allowed to proceed overnight without heating. The solvent is then evaporated under reduced pressure and the residue mixed with ice and made basic with concentrated sodium hydroxide. The mixture is extracted with chloroform and the chloroform layer washed with brine, dried (sodium sulfate) and evaporated under reduced pressure to give a white solid. Crystallization of the residue from chloroform gives 9.89 grams white crystals, melting point 140°C. to 143°C. The analytical sample is obtained from 2-propanol and has a melting point 140°C. to 143°C. Analysis calculated for C$_{10}$H$_{13}$NO: C, 73.59; H, 8.03; N, 8.58. Found: C, 73.47; H, 7.94; N, 8.96.

EXAMPLE 106

Preparation of N-(5,6,7,8-Tetrahydro-8-oxo-2-naphthyl)acetamide

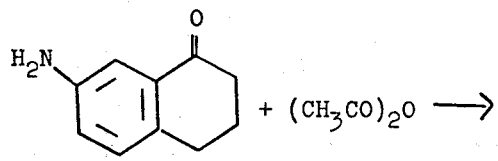

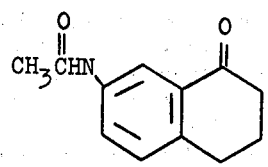

A mixture containing 1.6 grams (10 mmoles) of the amine in 10 ml. acetic anhydride and 5 ml. pyridine is stirred overnight at room temperature. The resultant precipitate is removed by filtration, washed with acetic anhydride and air-dried. The product is recrystallized from 95% ethanol to give analytically pure N-(5,6,7,8-tetrahydro-8-oxo-2-naphthyl)-acetamide, melting point 165°C. to 166°C.

EXAMPLE 107

Preparation of N-[5,6,7,8-Tetrahydro-8-(hydroxyimino)-2-naphthyl]acetamide

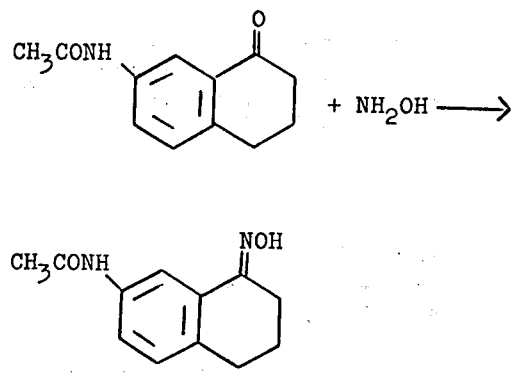

A mixture containing 50 grams (0.246 mole) of ketone, 48.4 grams (0.59 mole) of sodium acetate, 34.2 grams (0.492 mole) of hydroxylamine hydrochloride in 100 ml. of water and 100 ml. of 95% ethanol is stirred and heated at 75°C. for 1.5 hours. After standing overnight, the mixture is poured into water and the resulting precipitate removed by filtration, washed with water and air-dried to give 50.7 grams of oxime, melting point 209.5°C. to 210°C. (dec.). Recrystallization of a sample from acetic acid gives analytically pure oxime, melting point 205°C. to 206°C. (dec.).

EXAMPLE 108

Preparation of N-(8-Amino-5,6,7,8-tetrahydro-2-naphthyl)acetamide hydrochloride

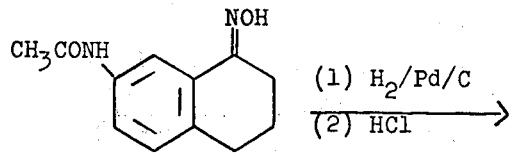

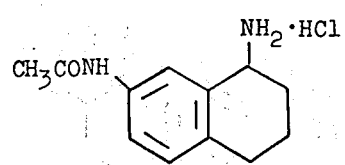

A suspension of 45 grams (0.206 mole) of oxime and 3.5 grams of 5% palladium-on-carbon in 180 ml. of 95% ethanol is shaken in an atmosphere of hydrogen at 3 atmospheres of pressure. Reduction is complete in 4.5 hours. The catalyst is removed by filtration and the solvent removed under reduced pressure to leave essentially pure N-(8-amino-5,6,7,8-tetrahydro-2-naphthyl)acetamido which has a melting point 124°C. to 129°C.

For further characterization, an aliquot of the amine is dissolved in acetonitrile and acidified with 6N hydrogen chloride in 2-propanol. The resulting precipitate is collected and recrystallized from aqueous ethanol to give analytically pure N-(8-amino-5,6,7,8-tetrahydro-2-naphthyl)acetamide hydrochloride, melting point 268°C. to 269°C.

EXAMPLE 109

Preparation of 1,2,3,4-Tetrahydro-1,7-naphthalenediamine dihydrochloride

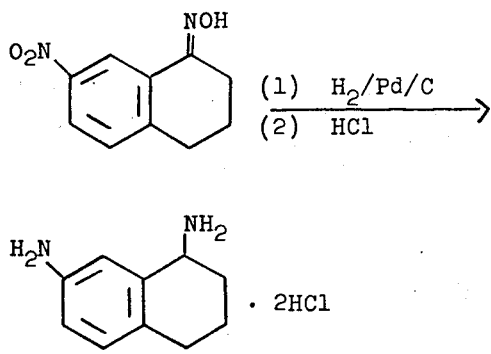

A solution containing 20.6 grams (0.1 mole) oxime in 150 ml. 95% ethanol is shaken in an atmosphere of hydrogen at 3 atmospheres pressure in the presence of 1.0 grams 5% palladium-on-carbon. The theoretical amount of hydrogen is absorbed in approximately 3 hours. The catalyst is removed by filtration and the filtrate acidified with 6N hydrogen chloride in 2-propanol. Evaporation of the solvent to a small volume and addition of ether precipitates the diamine dihydrochloride which is removed by filtration, washed with ether and air-dried, melting point 203°C. to 208°C. (dec.).

EXAMPLE 110

Preparation of 1-Methyl-3-(1,2α,3,4-tetrahydro-2β-iodo-1β-methyl-1-naphthyl)urea

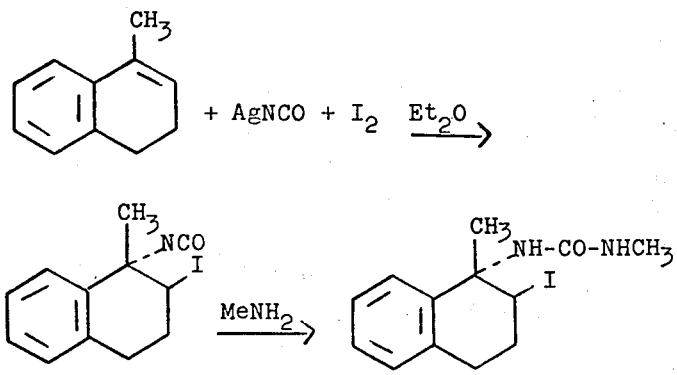

A mixture of 29.75 grams (0.206 mole) of olefin and 40.2 grams (0.268 mole) of AgNCO is stirred in 500 ml. of dry $Et_2O$ at −7°C. while 52.5 grams (0.206 mole) of $I_2$ is added at once. This is stirred at 0°C. to −10°C. for 1.25 hours and then at 10°C. to 15°C. for 1.5 hours. The mixture is then filtered through diatomaceous earth and the filter cake is washed thoroughly with ethyl ether. The filtrate is stirred in an ice bath and treated with 20 ml. of 40% aqueous methylamine to afford the iodourea, which was washed thoroughly with ethyl ether and water. This gave 50.03 grams (70.8%), melting point 122°C. to 123°C.

EXAMPLE 111

Preparation of 1-Methyl-3-(1,2,3,4-tetrahydro-1-methyl-1-naphthyl)urea

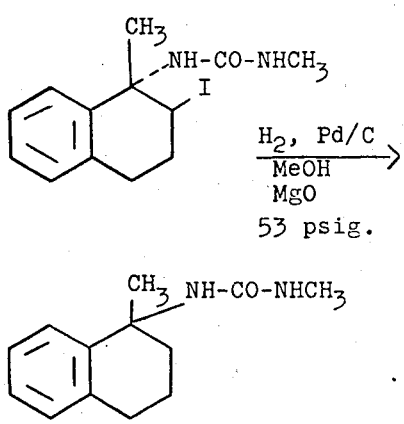

A mixture of 34.42 grams (0.1 mole) of iodourea, 5 grams of MgO, 7.52 grams of 5% Pd/C in 500 ml. of methanol is shaken in a Paar hydrogenator for 52 hours at which time the uptake was 6.5 psi. The mixture is filtered through diatomaceous earth under nitrogen atmosphere, the filter cake washed thoroughly with methanol and the filtrate was evaporated to dryness. The residue is dissolved in ethanol and ice is added to the solution until crystallization occurs. The mixture is cooled in ice and the solid is collected and washed well with cold 40% aqueous ethanol. This gives 15.03 grams of crude product (dried in vacuum oven at 70°C. to 90°C. for 2 hours), melting point 178°C. to 181°C. A second crop of 1.92 grams, melting point starting at 160°C., is obtained by concentration of the mother liquor. Recrystallization of the first crop from acetone-hexane affords 11.52 grams, melting point 185°C. to 187.5°C.; a second crop of 1.58 grams, melting point 183°C. to 186°C., is obtained from this. Two recrystallizations of the original second crop is 1.13 grams, melting point 183°C. to 186°C. The combined yield was 14.23 grams (65.5%), melting point 184°C. to 187°C.

EXAMPLE 112

Preparation of 1,2,3,4-Tetrahydro-1-naphthyl isothiocyanate

Method A

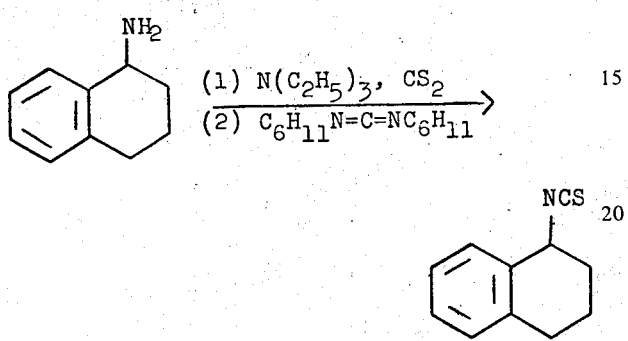

To a stirred solution of 0.01 mole of 1,2,3,4-tetrahydro-1-naphthylamine in ethyl acetate is added 0.01 mole of triethylamine and 0.011 mole of carbon disulfide. The mixture is stirred about one hour and then 0.01 mole of dicyclohexyl carbodiimide is added. The mixture is stirred overnight, and the mixture filtered to remove solid dicyclohexylthiourea. The filtrate is evaporated, and the residue is purified by dry column chromatography to give 1,2,3,4-tetrahydro-1-naphthyl isothiocyanate.

Method B

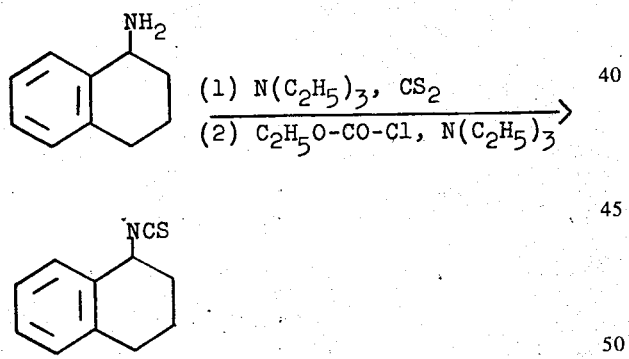

To a stirred solution of 0.01 mole of 1,2,3,4-tetrahydro-1-naphthylamine and 0.01 mole of triethylamine in chloroform is added a solution of 0.01 mole of carbon disulfide in chloroform. The reaction mixture is stirred about one hour, and then a solution of 0.01 mole of ethyl chloroformate in chloroform is added dropwise. After about one hour, 0.01 mole of triethylamine is added dropwise. The reaction is allowed to proceed for about 1 hour, and the solution is then washed with water, dilute hydrochloric acid solution, sodium bicarbonate solution and water. The organic phase is dried, and the solvent evaporated at reduced pressure to give the crude product.

EXAMPLES 113 through 132

Preparation of 1-Ethyl-3-(1,2,3,4-tetrahydro-1-naphthyl)thiourea

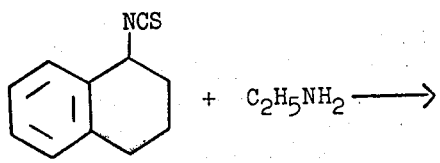

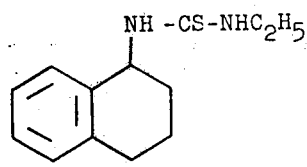

To a stirred solution of 0.01 mole of 1,2,3,4-tetrahydro-1-naphthyl isothiocyanate in tetrahydrofuran is added a solution of 0.011 mole of ethylamine in tetrahydrofuran. The reaction mixture is stirred overnight at room temperature, and the solvent then evaporated at reduced pressure to give material identical to that described in Example 87.

The thioureas listed in Table VI are prepared in an analogous way by the reaction of the appropriate amine, $R_1R_2NH$, and tetrahydronaphthyl isothiocyanate. Temperatures employed in this procedure range from 0°C. to 100°C.

Other aprotic solvents, e.g., ether, methylene chloride, chloroform, toluene and protic solvents such as methanol, ethanol, and the like, may be also used. Reaction of two equivalents of the tetrahydronaphthyl isothiocyanate with a diamine (e.g., $NH_2CH_2CH_2NH_2$) gives the bis-thiourea product.

TABLE VI

Compound Structure:

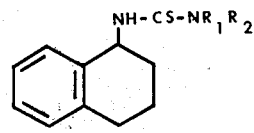

| Example Number | $R_1$ | $R_2$ |
|---|---|---|
| 114 | $CH_3$ | $CH_3$ |
| 115 | $C_2H_5$ | $C_2H_5$ |
| 116 | $n\text{-}C_4H_9$ | $n\text{-}C_4H_9$ |
| 117 | $n\text{-}C_4H_9$ | H |
| 118 | $n\text{-}C_{12}H_{25}$ | H |
| 119 | $CH_2CH=CH_2$ | H |
| 120 | $CO-OC_2H_5$ | H |
| 121 | ⟨cyclopentyl⟩ | H |
| 122 | ⟨cyclohexyl⟩ | H |
| 123 | $CH_2C_6H_5$ | H |
| 124 | $CH_2CH_2OH$ | H |
| 125 | ⟨-C₆H₄-Cl⟩ | H |
| 126 | ⟨-C₆H₄-OCH₃⟩ | H |

TABLE VI-continued

Compound Structure:

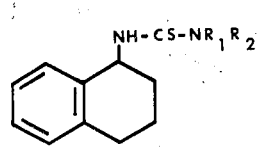

| Example Number | $R_1$ | $R_2$ |
|---|---|---|
| 127 | -CH$_2$-(4-pyridyl) | H |
| 128 | N(CH$_3$)$_2$ | H |
| 129 | NH—CO—OCH$_3$ | H |
| 130 | NH—C$_6$H$_5$ | H |
| 131 | (5,6,7,8-tetrahydro-2-naphthyl) | H |
| 132 | -CH$_2$CH$_2$NH-CO-NH-(1,2,3,4-tetrahydro-1-naphthyl) | H |

EXAMPLES 133 through 138

Preparation of
1-Methoxy-3-(1,2,3,4-tetrahydro-1-naphthyl)-thiourea

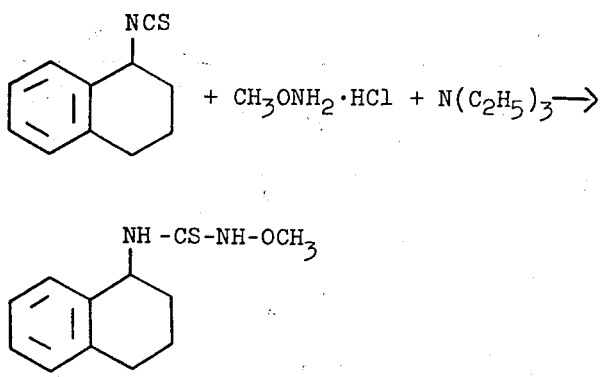

To an ice-cold, stirred mixture of 0.02 mole of methoxyamine hydrochloride and methylene chloride is added 0.02 mole of triethylamine. The mixture is then allowed to warm to about 15° C. to 25° C. while a solution of 0.01 mole of 1,2,3,4-tetrahydro-1-naphthyl isothiocyanate in methylene chloride is added dropwise. The mixture is stirred overnight at room temperature and then filtered. The filtrate is washed with water, dried (sodium sulfate), and the solvent evaporated at reduced pressure to give the title compound.

The alkoxy- and hydroxythioureas, described in Table VII below, are prepared in a similar manner using the appropriate hydroxyl- or alkoxyamine (1.0 to 2.0 equivalents) and tetrahydronaphthyl isothiocyanate. Other aprotic and protic solvents such as tetrahydrofuran, acetone, methanol, and the like, may be used in this procedure. The conversion of the alkoxy- and hydroxylamine salts to the corresponding free bases may be accomplished with other bases such as potassium carbonate, sodium carbonate, as well as other trialkylamines.

TABLE VII

Compound Structure:

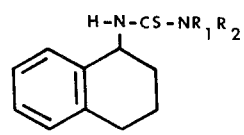

| Example Number | $R_1$ | $R_2$ |
|---|---|---|
| 134 | OCH$_3$ | CH$_3$ |
| 135 | OH | H |
| 136 | OH | CH$_3$ |
| 137 | OC$_2$H$_5$ | H |
| 138 | OCH$_2$C$_6$H$_5$ | H |

EXAMPLE 139

Mouse Growth Regulant Tests

CFI female mice from Carworth Farm are received when they are six weeks old. They are housed ten to a cage in air-conditioned rooms (72° F. to 76° F.) with automatically controlled lights, 14 hours on and 10 hours off. The basal diet used in these studies is Purina Laboratory Chow (see description below), which is supplied ad libitum. Water is also allowed ad libitum.

Thirteen days after arrival, the mice are weighed in groups of ten and assigned at ramdom to the different treatments. The concentration of the different compounds in the diet is indicated in the enclosed Tables. Twelve days later the mice are weighed again and the experiment terminated. At least three cages (30 mice) of untreated controls are included in each test. Test data are provided in Tables VIII and IX below. Data reported in Table VIII relates to compounds of the present invention which are preferred as animal growth promoting agents. Data for other compounds of the invention which are also active as animal growth promoting agents are given in Table IX.

Diet

| GUARANTEED ANALYSIS | |
|---|---|
| Crude protein not less than | 23.0% |
| Crude fat not less than | 4.5% |
| Crude fiber not more than | 6.0% |
| Ash not more than | 9.0% |

INGREDIENTS

Meat and bone meal, dried skimmed milk, wheat germ meal, fish meal, animal liver meal, dried beet pulp, ground extruded corn, ground oat groats, soybean meal, dehydrated alfalfa meal, cane molasses, animal fat preserved with BHA, vitamin B$_{12}$ supplement, calcium pantothenate, choline chloride, folic acid, riboflavin supplement, brewers' dried yeast, thiamin, niacin, vitamin A supplement, D activated plant sterol, vitamin E supplement, calcium carbonate, dicalcium phosphate, iodized salt, ferric ammonium citrate, iron oxide, manganous oxide, cobalt carbonate, copper oxide, zinc oxide.

TABLE VIII

Mouse Growth Regulant Test with Compounds having the Structure:

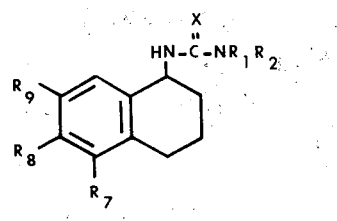

| X | $R_1$ | $R_2$ | $R_7$ | $R_8$ | $R_9$ | Dietary Level ppm | % Weight Gain Over Controls |
|---|---|---|---|---|---|---|---|
| O | H | $C_2H_5$ | H | H | H | 100 | 21.4 |
|   |   |   |   |   |   | 200 | 43.0 |
|   |   |   |   |   |   | 400 | 64.6 |
| O | $CH_3$ | H | H | H | H | 50 | 20.2 |
|   |   |   |   |   |   | 100 | 87.1 |
|   |   |   |   |   |   | 200 | 66.8 |
|   |   |   |   |   |   | 400 | 87.1 |
| O | $-OCH_3$ | $CH_3$ | H | H | H | 200 | 51.6 |
| O | H | $-C_3H_7-n$ | H | H | H | 100 | 65.3 |
|   |   |   |   |   |   | 200 | 49.5 |
|   |   |   |   |   |   | 400 | 80.4 |
| S | $C_2H_5-$ | H | H | H | H | 100 | 45.0 |
|   |   |   |   |   |   | 200 | 30.0 |
|   |   |   |   |   |   | 400 | 84.9 |
| O | $CH_3$ | $CH_3$ | H | H | H | 100 | 22.5 |
|   |   |   |   |   |   | 200 | 47.3 |
|   |   |   |   |   |   | 400 | 66.1 |
| O | H | $-\underset{\underset{CH_3}{\mid}}{CH}-C_2H_5$ | H | H | H | 100 | 37.5 |
|   |   |   |   |   |   | 200 | 46.0 |
|   |   |   |   |   |   | 400 | 92.4 |
| O | $C_2H_5$ | $C_2H_5$ | H | H | H | 200 | 0.6 |
| O | $C_2H_5$ | H | H | $-OCH_3$ | H | 200 | 20.9 |
| O | H | H | $-OCH_3$ | H | H | 200 | 82.4 |
| O | $C_2H_5$ | H | $-OCH_3$ | H | H | 200 | 21.7 |
| O | H | $-CH_2C_6H_5$ | H | H | H | 200 | 48.7* |
| O | H | $CH_3$ | $-CH_3$ | H | $-CH_3$ | 200 | 20.9 |
| O | H | $C_2H_5$ | H | $-CH_3$ | $-CH_3$ | 200 | 1.4 |
| O | H | H | $-CH_3$ | H | $-CH_3$ | 200 | 112.2 |
| O | $CH_3$ | H | $-CH_3$ | H | $-CH_3$ | 200 | 95.9 |
| O | H | $OCH_3$ | H | H | H | 100 | 39.6 |
|   |   |   |   |   |   | 200 | 61.6 |
|   |   |   |   |   |   | 400 | 107.9 |
| O | $C_2H_5$ | H | H | H | $-CH(CH_3)_2$ | 200 | 92.0 |
| O | H | $CH_3$** | H | H | H | 200 | 129.5 |
| O | H | $-OCH_2C_6H_5$ | H | H | H | 400 | 71.7* |

*Average 2 replicates.
**(S) - Optical isomer.

TABLE IX

Mouse Growth Regulant Test with Compounds having the Structure:

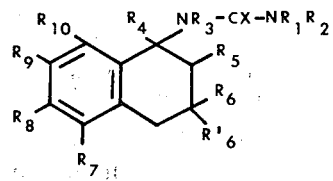

| X | $R_1$ | $R_2$ | $R_3$ | $R_4$ | $R_5$ | $R_6$ | $R_7$ | $R_8$ | $R'_6$ $R_9$ | $R_{10}$ | Dietary Level ppm | % Weight Gain Over Controls |
|---|---|---|---|---|---|---|---|---|---|---|---|---|
| O | $C_6H_{11}$ | H | H | H | H | H | H | H | H | H | 100 | 16.4 |
| O | $-C_6H_4-OCH_3-p$ | H | H | H | H | H | H | H | H | H | 200 | 26.5 |
| O | $-CH_2-\underset{\underset{O}{\parallel}}{C}-O-C_2H_5$ | H | $CH_3$ | H | H | H | H | H | H | H | 200 | 60.3 |

TABLE IX-continued

Mouse Growth Regulant Test with Compounds having the Structure:

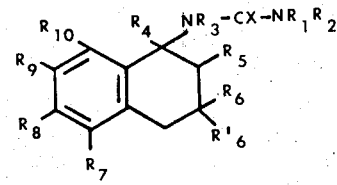

| X | $R_1$ | $R_2$ | $R_3$ | $R_4$ | $R_5$ | $R_6$ | $R'_6$ | $R_7$ | $R_8$ | $R_9$ | $R_{10}$ | Dietary Level ppm | % Weight Gain Over Controls |
|---|---|---|---|---|---|---|---|---|---|---|---|---|---|
| O | $CH_3$ | H | H | H | H | H | H | H | H | $CH_3-\overset{O}{\underset{\|}{C}}-NH-$ | H | 200 | 15.7 |
| O | $C_2H_5$ | H | H | H | H | H | H | H | H | $CH_3-\overset{O}{\underset{\|}{C}}-NH-$ | H | 200 | 62.6 |
| O | H | H | H | H | H | H | H | H | H | $CH_3-\overset{O}{\underset{\|}{C}}-NH-$ | H | 200 | 27.8 |
| O | $C_6H_{13}-n$ | H | H | H | H | H | H | H | H | $CH_3-\overset{O}{\underset{\|}{C}}-NH-$ | H | 200 | 6.4 |
| O | $C_{12}H_{25}-n$ | H | H | H | H | H | H | $CH_3O-$ | H | H | H | 200 | 0.6 |
| O | $-CH_2CH_2OH$ | H | H | H | H | H | H | H | H | H | H | 200 | 13.7 |
| O | $C_2H_5$ | H | $-CH(CH_3)_2$ | H | H | H | H | H | H | $CH_3-\overset{O}{\underset{\|}{C}}-NH-$ | H | 200 | 92.6 |
| O | $CH_3$ | H | $-CH(CH_3)_2$ | H | H | H | H | H | H | $CH_3-\overset{O}{\underset{\|}{C}}-NH-$ | H | 200 | 23.1 |
| O | $C_2H_5$ | H | H | H | H | H | H | H | H | $\underset{H-\overset{\|}{\underset{\|}{C}}-NH-}{\overset{C_2H_5-N-}{\overset{\|}{\underset{O}{}}}}$ | H | 200 | 87.0 |
| O | $CH_3$ | H | H | H | H | H | H | H | H | $\underset{H-\overset{\|}{\underset{\|}{C}}-NH-}{\overset{CH_3-N-}{\overset{\|}{\underset{O}{}}}}$ | H | 400 | 23.0 |
| O | 2-pyridyl | H | H | H | H | H | H | H | H | H | H | 200 | 67.0 |
| O | OH | H | H | H | H | H | H | H | H | H | H | 400 | 0.9 |
| O | $-C_{12}H_{25}-n$ | H | H | H | H | H | H | H | H | $-CH(CH_3)_2$ | H | 400 | 2.2 |
| O | $-CH_2-CH=CH_2$ | H | H | H | H | H | H | H | H | H | H | 400 | 38.0 |
| O | $-CH_2$-(4-pyridyl) | H | H | H | H | H | H | H | H | H | H | 400 | 27.4 |
| O | $-CH_2$-(4-pyridyl) | H | H | H | H | H | H | H | H | H | H | 400 | 42.4 |
| O | $-CH_2$-(1-methylpyridinium $ClO_4^-$) | H | H | H | H | H | H | H | H | H | H | 400 | 17.0 |
| O | 4,6-dichloropyrimidin-2-yl | H | H | H | H | H | H | H | H | H | H | 200 | 58.4 |
| O | H | H | H | H | H | Cl | H | H | H | H | H | 400 | 5.6 |
| O | 2-oxoimidazolidin-1-yl | | | H | H | H | H | H | H | H | H | 400 | 23.0 |
| O | $-CH_2OCH_3$ | H | H | H | H | H | H | H | H | H | H | 400 | 30.0 |
| O | $C_2H_5$ | H | OH | H | H | H | H | H | H | H | H | 400 | 18.6 |
| O | $CH_3$ | H | H | $CH_3$ | H | H | H | H | H | H | H | 400 | 16.9 |
| O | $CH_3$ | H | H | $CH_3$ | I | H | H | H | H | H | H | 400 | 11.0 |
| S | $CH_3$ | H | OH | H | H | H | H | H | H | H | H | 400 | 0.9 |
| O | OH | $CH_3$ | H | H | H | H | H | H | H | H | H | 400 | —43.3 |
| O | $-OC_2H_5$ | H | H | H | H | H | H | H | H | H | H | 400 | 84.4 |

EXAMPLE 140

The preemergence herbicidal activity of the compounds of the invention is demonstrated by the following tests in which the seeds of a variety of monocotyledonous and dicotyledonous plants are separately mixed with potting soil and planted on top of approximately 1 inch of soil in separate pint cups. After planting, the cups are sprayed with a selected aqueous acetone solution containing test compound in sufficient quantity to provide the equivalent of about 1.0 pound to 10 pounds per acre of test compound per cup. The treated cups are then placed on greenhouse benches and cared for in accordance with greenhouse procedures. Three weeks after treatment, the tests are terminated and each cup is examined and rated according to the rating system set forth below. Results are reported in the Table X below.

| Rating System: | % Difference in Growth from the Check* |
|---|---|
| 0 - no effect | 0 |
| 1 - possible effect | 1-10 |
| 2 - slight effect | 11-25 |
| 3 - moderate effect | 26-40 |
| 5 - definite injury | 41-60 |
| 6 - herbicidal effect | 61-75 |
| 7 - good herbicidal effect | 76-90 |
| 8 - approaching complete kill | 91-99 |
| 9 - complete kill | 100 |

4 - abnormal growth, i.e., a definite physiological malformation but with an over-all effect less than a 5 on the rating scale.
*Based on visual determination of stand, size, vigor, chlorosis, growth malformation and over-all plant appearance.

TABLE X

Preemergence Herbicidal Activity

| Compound of Example Number | Treatment lb/Acre | Annual Weeds | | | | | | | | | |
|---|---|---|---|---|---|---|---|---|---|---|---|
| | | LA | MU | PI | RW | MG | BA | CR | GRF | WO | VL |
| 1 | 9 | 8 | 7 | 6 | 3 | 9 | 3 | 9 | 7 | 2 | 6 |
| | 3 | 7 | 6 | 9 | 0 | 3 | 1 | 7 | 5 | 1 | 1 |
| 14 | 10 | 8 | 7 | 8 | 6 | 0 | 7 | 8 | 7 | 2 | 2 |
| | 4 | 7 | 3 | 2 | 0 | 2 | 3 | 8 | 6 | 1 | 7 |
| 15 | 10 | 8 | 8 | 0 | 0 | 9 | 7 | 9 | 9 | 2 | 3 |
| | 4 | 7 | 8 | 2 | 2 | 9 | 7 | 9 | 8 | 3 | 2 |
| | 1 | 2 | 0 | 0 | 0 | 9 | 2 | 5 | 2 | 0 | 0 |
| 85 | 10 | 7 | 9 | 8 | 8 | 7 | 6 | 7 | 7 | 2 | 9 |
| | 4 | 8 | 9 | 7 | 3 | 9 | 2 | 8 | 0 | 2 | 9 |
| | 1 | 6 | 8 | 3 | 0 | 2 | 0 | 1 | 0 | 1 | 5 |
| 13 | 10 | 8 | 7 | 7 | 8 | 5 | 5 | 8 | 7 | 8 | 7 |
| | 4 | 5 | 5 | 7 | 2 | 8 | 5 | 8 | 6 | 1 | 7 |
| 87 | 10 | 9 | 8 | 8 | 6 | 8 | 3 | 8 | 3 | 0 | 7 |
| 86 | 10 | 9 | 9 | 9 | 9 | 9 | 8 | 9 | 9 | 5 | 9 |
| | 3 | 7 | 9 | 2 | 7 | 0 | 3 | 7 | 6 | 0 | 6 |
| 65 | 10 | 3 | 0 | 0 | 0 | 0 | 8 | 8 | 9 | 0 | |
| | 9 | 2 | 0 | 0 | 0 | 1 | 9 | 7 | 8 | 2 | 7 |
| 71 | 10 | 9 | 8 | 8 | 3 | 7 | 0 | 2 | 0 | 2 | 9 |
| | 9 | 9 | 8 | 8 | 8 | 6 | 3 | 7 | 5 | 3 | 9 |
| | 3 | 8 | 6 | 5 | 2 | 1 | 0 | 0 | 0 | 0 | 2 |
| 37 | 10 | 9 | 9 | 9 | 9 | 9 | 7 | 9 | 5 | 5 | 9 |
| | 4 | 9 | 9 | 9 | 3 | 8 | 5 | 7 | 1 | 3 | 9 |
| | 1 | 9 | 5 | 5 | 0 | 0 | 0 | 0 | 0 | 0 | 3 |
| 41 | 10 | 8 | 5 | 5 | 5 | 2 | 1 | 5 | 5 | 1 | 2 |
| 100 | 10 | 9 | 8 | 6 | 8 | 9 | 7 | 6 | 5 | 0 | 8 |
| | 9 | 9 | 2 | 5 | 7 | 7 | 6 | 2 | 2 | 5 | 9 |
| | 3 | 9 | 0 | 0 | 9 | 0 | 0 | 0 | 0 | 1 | 0 |
| 45 | 10 | 9 | 8 | 5 | 0 | 0 | 5 | 7 | 5 | 0 | 5 |
| 31 | 9 | 2 | 0 | 0 | 0 | 1 | 9 | 7 | 8 | 2 | 7 |
| | 3 | 0 | 0 | 0 | 0 | 0 | 5 | 5 | 6 | 1 | 0 |
| 55 | 9 | 9 | 9 | 9 | 7 | 2 | 5 | 7 | 6 | 1 | 9 |
| | 3 | 3 | 0 | 0 | 5 | 1 | 0 | 2 | 2 | 0 | 9 |
| 36 | 10 | 7 | 8 | 2 | 2 | 1 | 7 | 8 | 6 | 1 | 3 |
| 73 | 10 | 9 | 8 | 9 | 3 | 0 | 0 | 3 | 0 | 0 | 9 |
| | 4 | 9 | 9 | 8 | 0 | 0 | 0 | 4 | 4 | 1 | 9 |
| 21 | 10 | 9 | 9 | 9 | 9 | 9 | 7 | 9 | 5 | 5 | 9 |
| | 4 | 9 | 9 | 9 | 3 | 8 | 5 | 7 | 1 | 3 | 9 |
| | 1 | 9 | 5 | 5 | 0 | 0 | 0 | 0 | 0 | 0 | 3 |
| 52 | 10 | 9 | 6 | 0 | 8 | 7 | 3 | 5 | 5 | 2 | 9 |
| 101 | 10 | 9 | 8 | 0 | 0 | 3 | 7 | 9 | 8 | 0 | 7 |
| | 9 | 9 | 8 | 6 | 9 | 3 | 7 | 9 | 9 | 5 | 9 |
| | 3 | 9 | 9 | 0 | 9 | | 1 | 7 | 7 | 1 | 7 |
| 102 | 10 | 9 | 8 | 6 | 8 | 9 | 7 | 6 | 5 | 0 | 8 |
| | 9 | 9 | 2 | 5 | 7 | 7 | 6 | 2 | 2 | 5 | 9 |
| | 3 | 9 | 0 | 0 | 9 | 0 | 0 | 0 | 0 | 1 | 0 |
| 95 | 10 | 8 | 2 | 3 | 2 | 0 | 8 | 8 | 6 | 0 | 0 |
| | 9 | 3 | 0 | 0 | 0 | 1 | 4 | 4 | 7 | 2 | 4 |

Plant Abbreviations:
- LA - Lambsquarters
- MU - Mustard
- PI - Pigweed
- BA - Barnyard grass
- CR - Crab grass
- GRF - Green foxtail
- WO - Wild Oats
- RW - Ragweed
- MG - Morning-glory
- VE - Velvet leaf

EXAMPLE 141

The postemergence herbicidal activity of the preferred compounds of the present invention is demonstrated by the following tests, wherein a variety of monocotyledonous and dicotyledonous plants are treated with test compounds dispersed in aqueous acetone mixtures. In the tests, seedling plants are grown in jiffy flats for about two weeks. The test compounds are dispersed in 50/50 acetone/water mixtures in sufficient quantity to provide the equivalent of about 1.0 pound to 10 pounds per acre of active compound when applied to the plants through a spray nozzle operating at 40 psi for a predetermined time. After spraying, the plants are placed on greenhouse benches and are cared for in the usual manner, commensurate with conventional greenhouse practices. Two weeks after treatment, the seedling plants are examined and rated according to the rating system provided in the preceding example. The data obtained are reported in the Table below.

TABLE XI

Postemergence Herbicidal Activity

| Compound of Example Number | Treatment lb/Acre | Annual Weeds | | | | | | | | | |
|---|---|---|---|---|---|---|---|---|---|---|---|
| | | LA | MU | PI | RW | MG | BA | CR | GRF | WO | VL |
| 86 | 9 | 9 | 9 | 9 | 8 | 6 | 9 | 9 | 9 | 2 | 9 |
|    | 3 | 9 | 9 | 6 | 2 | 1 | 7 | 8 | 8 | 1 | 5 |
|    | 1 | 7 | 2 | 1 | 1 | 0 | 3 | 1 | 0 | 0 | 2 |
| 73 | 10 | 8 | 5 | 9 | 3 | 3 | 1 | 2 | 2 | 0 | 8 |
|    | 4 | 8 | 7 | 5 | 0 | 1 | 0 | 0 | 0 | 0 | 1 |
| 21 | 10 | 9 | 3 | 3 | 0 | 7 | 0 | 0 | 0 | 0 | 5 |
| 52 | 10 | 8 | 1 | 1 | 0 | 3 | 2 | 1 | 1 | 1 | 6 |
| 55 | 10 | 8 | 2 | 6 | 0 | 5 | 2 | 1 | 1 | 0 | 6 |

We claim:

1. A compound of the formula:

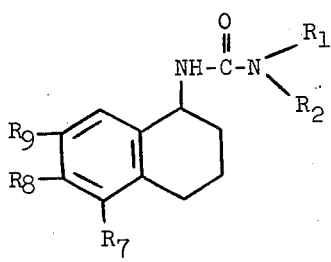

wherein $R_1$ is selected from the group consisting of alkyl $C_1$–$C_4$, alkoxy $C_1$–$C_4$, benzyl and benzyloxy; $R_2$ is selected from the group consisting of hydrogen and alkyl $C_1$–$C_4$; $R_7$ and $R_8$ are each individually selected from the group consisting of hydrogen, alkyl $C_1$–$C_4$ and alkoxy $C_1$–$C_4$; and $R_9$ is selected from the group consisting of hydrogen and alkyl $C_1$–$C_4$, with the proviso that at least one of $R_7$, $R_8$, and $R_9$ is hydrogen.

2. A compound of the formula:

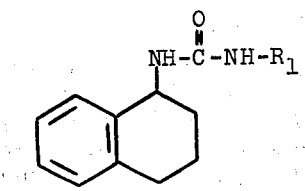

wherein $R_1$ is alkyl $C_1$–$C_6$.

3. The compound according to claim 2 wherein $R_1$ is methyl.

4. The compound according to claim 2 wherein $R_1$ is n-propyl.

5. The compound according to claim 1 wherein $R_1$ is methyl; $R_2$ and $R_8$ are each hydrogen; and $R_7$ and $R_9$ are each methyl.

6. An optically active compound of the formula:

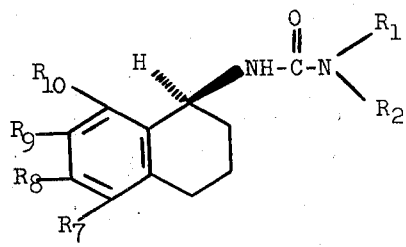

wherein $R_1$ is selected from the group consisting of alkyl $C_1$–$C_4$, alkoxy $C_1$–$C_4$, benzyl and benzyloxy; $R_2$ is selected from the group consisting of hydrogen and alkyl $C_1$–$C_4$; and $R_7$, $R_8$, $R_9$ and $R_{10}$ are each individually selected from the group consisting of hydrogen, alkyl $C_1$–$C_4$ and alkoxy $C_1$–$C_4$ with the proviso that at least two of $R_7$ to $R_{10}$ must be hydrogen.

* * * * *